United States Patent [19]

Buckler et al.

[11] Patent Number: 4,794,079

[45] Date of Patent: Dec. 27, 1988

[54] DETERMINATION OF HYDROGEN PEROXIDE USING FLUOROGENIC DIHYDROQUINOLONE AND DIHYDROCOUMARIN INDICATORS

[75] Inventors: Robert T. Buckler, Edwardsburg, Mich.; Robert P. Hatch, Elkhart, Ind.

[73] Assignee: Miles Inc., Elkhart, Ind.

[21] Appl. No.: 781,747

[22] Filed: Sep. 30, 1985

Related U.S. Application Data

[62] Division of Ser. No. 594,242, Mar. 27, 1984, Pat. No. 4,558,130.

[51] Int. Cl.[4] .............................................. C12Q 1/28
[52] U.S. Cl. ...................................... 435/28; 424/7.1; 549/288; 549/289; 546/156; 546/158
[58] Field of Search .......................... 435/28; 424/7.1; 549/288, 289; 546/156, 158, 66

[56] References Cited

U.S. PATENT DOCUMENTS

| | | | |
|---|---|---|---|
| 4,065,456 | 12/1977 | Nakagawa et al. | 546/157 |
| 4,105,665 | 8/1978 | Harnisch | 546/66 |
| 4,391,905 | 7/1983 | Bauer | 435/14 |
| 4,394,444 | 7/1983 | Cameron et al. | 435/11 |
| 4,447,542 | 5/1984 | Gantzer | 436/66 |
| 4,558,130 | 12/1985 | Buckler et al. | 435/28 X |

OTHER PUBLICATIONS

J. Chem. Soc. (C), 1969, pp. 183–188, "The Schmidt Reaction with Benzocycloalkenones"; M. Tomita, S. Minami.

J. Chem. Soc. (C), 1969, pp. 1749–1751, "Coumarin and Related Compounds. Part VIII.[1] Aluminium Chloride-catalysed Reactions of Phenols with Methyl Methacrylate. A Ready Synthesis of 6-Methylfuro[3,2-α] Coumarin and 7-Hydroxy-3-Methyl-Coumarin" A. K. D. Gupta; R. M. Chatterje and K. R. Das.

J. Indian Chem. Soc., vol. 47, #10 (1970) 1017–1018, "A Novel Approach to Phenylcoumarins" A. K. Das Gupta and M. S. Paul.

Chem. Absts., vol. 87, 1977, pp. 533–534 87:68181m.

J. Heterocyclic Chem., 20,493 (1983), "An Efficient Synthesis of Trans-Hexahydrochroman-7-one".

*Primary Examiner*—Robert J. Warden
*Assistant Examiner*—Jack Spiegel
*Attorney, Agent, or Firm*—Daniel W. Collins

[57] ABSTRACT

Fluorogenic indicator compounds responsive to the presence of hydrogen peroxide and methods and test compositions for determining hydrogen peroxide in a test sample. Preferred indicator compounds are 3,4-dihydrocoumarin derivatives and 3,4-dihydro-2-quinolone derivatives, especially those having a dialkylamino group at the 7-position. Such particularly preferred compounds are of the formula:

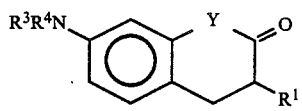

wherein $R^1$ is hydrogen, cyano, or $-COOR^6$, $-CONHR^6$ or $-CON(R^6)_2$ where $R^6$ is hydrogen, alkyl, alkenyl, or aryl; $R^3$ and $R^4$ are lower alkyl; and Y is $=O$ or $=N-R^5$ where $R^5$ is hydrogen or lower alkyl. The indicator compounds yield highly fluorescent products upon oxidation by hydrogen peroxide in the presence of a peroxidatively active substance and are useful in analytical systems which generate hydrogen peroxide in response to an analyte under determination in a test sample.

20 Claims, 6 Drawing Sheets

DETERMINATION OF HYDROGEN PEROXIDE USING FLUOROGENIC DIHYDROQUINOLONE AND DIHYDROCOUMARIN INDICATORS

This is a division of application Ser. No. 594,242 filed Mar. 27, 1984, now U.S. Pat. No. 4,558,130.

BACKGROUND OF THE INVENTION

1. Field of the Invention

The present invention relates to optical indicator compounds, and the methods for their preparation and use, which provide optical signals upon contact with oxidants, particularly hydrogen peroxide. In particular, the invention relates to fluorogenic indicators for hydrogen peroxide and their use in analytical systems, such as diagnostic test systems, which are based on the generation and detection of hydrogen peroxide in response to the analyte under determination.

2. Description of the Prior Art

Many analytical systems involve the measurement of an oxidative substance as the ultimately detected substance. The analyte under determination may itself be such oxidant or the analyte may participate in a chemical, biological, immunological, or the like reaction that produces or destroys a measurable oxidant. These oxidants include substances such as hydrogen peroxide, ozone, periodates, peracids, and superoxides.

In particular, the determination of oxidative enzyme activity is important in analytical chemistry and biochemistry because of its usefulness in clinical diagnostic systems. Among the more commonly studied oxidative enzymes are the oxidases which produce hydrogen peroxide, such as glucose oxidase, xanthine oxidase, and cholesterol oxidase. The hydrogen peroxide generated by the action of such enzymes on their substrates is generally quantitated by oxidation-reduction reactions with various types of optical indicators, usually in the presence of peroxidase. One of the most sensitive means for quantitating hydrogen peroxide is by the use of fluorogenic peroxidase substrates which yield fluorescent products upon peroxidase-catalyzed reaction with hydrogen peroxide.

The literature contains relatively few examples of fluorogenic peroxidase substrates. Some such indicators that have been reported in the literature are homovanillic acid, 3-(p-hydroxyphenyl)propionic acid, 4-amino-1H-1,5-benzodiazepine-3-carbonitrile, and diacetyldichlorofluorescein [K. Zaitsu and Y. Ohkura, Anal. Biochem. 109: 109(1980), H. Corrodi and B. Weidinius, Acta Chem. Scand. 19: 1854(1965), Y. Okamoto et al, Chem. Pharm. Bull. 28: 2325(1980), A. S. Keston and R. Brandt, Anal. Biochem. 11: 1(1965), and U.S. Pat. No. 4,269,938]. The fluorometric determination of hydrogen peroxide has also been accomplished using the fluorescent compound 6-methoxy-7-hydroxy-1,2-benzopyrone which is oxidized to a nonfluorescent product [W. A. Andreae, Nature 175: 859(1955)], and by utilizing a coupling reaction between a hydrogen donor and O-alkylated-7-hydroxy coumarins [European Pat. Appln. No. 82101947].

Applicants' copending U.S. patent application Ser. No. 475,200, filed Mar. 14, 1983, concerns optical indicator chalcogen (selenide or sulfide) compounds responsive to oxidants such as hydrogen peroxide. Upon oxidation the resulting intermediate undergoes spontaneous elimination of the chalcogen residue to yield a signal compound providing an optical signal such as fluorescence. Preferred indicators are 3-chalcogen-3,4-dihydrocoumarins and 3-chalcogen-3,4-dihydro-2-quinolones.

SUMMARY OF THE INVENTION

The present invention provides a novel class of fluorogenic indicator compounds responsive to hydrogen peroxide. Upon oxidation by hydrogen peroxide, preferably in the presence of a peroxidatively active substance such as peroxidase, the present, substantially nonfluorescent compounds yield highly fluorescent reaction products. Therefore, the present invention provides highly sensitive indicators for the detection of hydrogen peroxide and for use in analytical systems wherein hydrogen peroxide is generated or consumed as a function of the presence of an analyte of interest.

The present compounds are 3,4-dihydroquinolones and 3,4-dihydrocoumarins principally of the general formula:

(A)

wherein $R^1$ is hydrogen, alkyl, alkenyl, aryl, or an electron withdrawing group; $R^2$ is hydroxyl or $-NR^3R^4$ where $R^3$ and $R^4$, which can be the same or different, are hydrogen, alkyl, alkenyl, or aryl; and Y is $=O$ or $=N-R^5$ where $R^5$ is hydrogen or lower alkyl.

Figure 1:
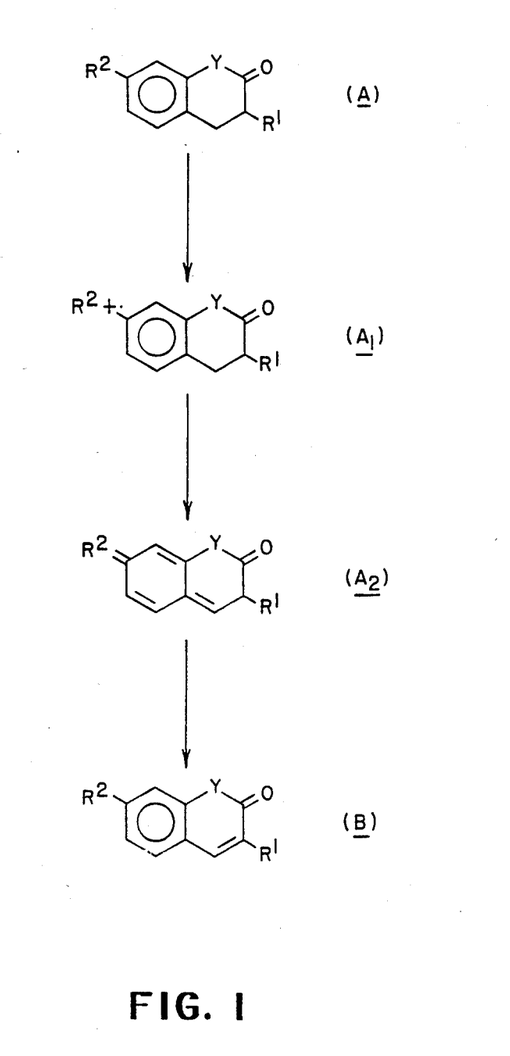
FIGS. 1 and 2 are proposed reaction mechanisms for oxidation of the present compounds generally and the preferred dialkylamino derivatives, respectively, as discussed above.

Upon oxidation by hydrogen peroxide in the presence of a peroxidatively active substance, a double bond is generated between the 3 and 4-positions yielding a fluorescent product. The process by which the double bond is introduced is believed to follow the series of steps depicted in FIG. 1 of the drawings. The initial step is believed to be a first oxidation of the heteroatom at the 7-position (the $R^2$ substituent) to a radical cation ($A_1$), followed by loss of a benzylic hydrogen atom to produce a dehydrogenated aromatic intermediate ($A_2$). The proton at the 3-position is then lost to introduce the double bond, yielding fluorescent quinolones and coumarins (B):

(B)

wherein $R^1$, $R^2$, and Y are as described above.

Figure 2:
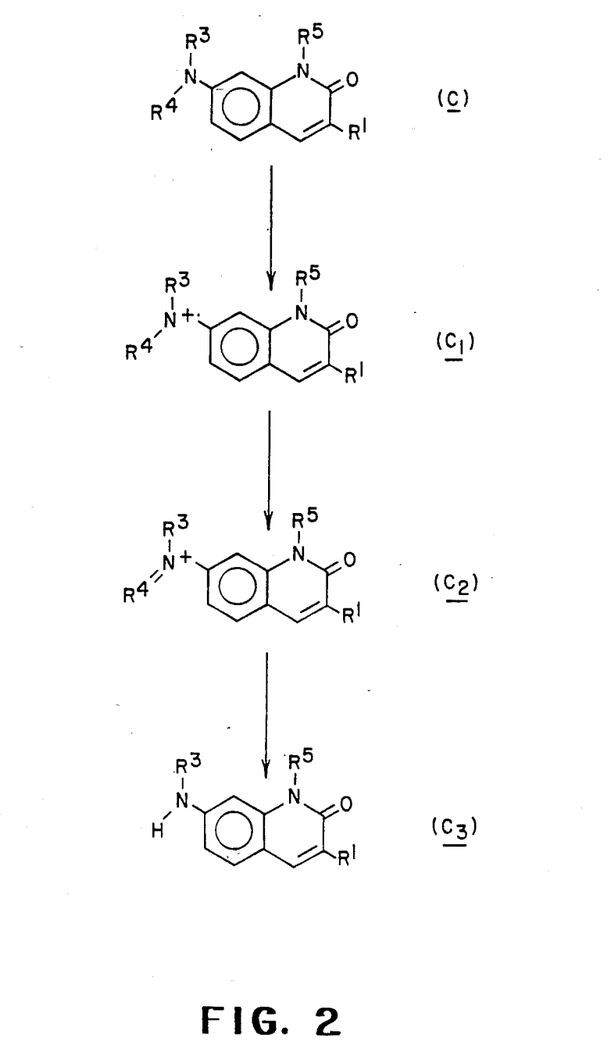

Particularly preferred indicator compounds are the 7-dialkylamino derivatives of formula (A) where $R^2$ is $-NR^3R^4$ and $R^3$ and $R^4$ are both lower alkyl, same or different, and preferably are both methyl, and Y is $=N-R^5$ where $R^5$ is hydrogen or lower alkyl. Such preferred compounds are believed to undergo a second oxidation as depicted in FIG. 2 of the drawings. The 7-dialkyamino-quinolone and -coumarin products (C) formed upon oxidation by hydrogen peroxide oxidize a second time at the heteroatom at the 7-position ($R^2$ substituent) to a radical cation ($C_1$), followed by loss of a hydrogen atom adjacent to the nitrogen to form an intermediate immonium ion ($C_2$). Hydrolysis then yields a new monoalkylamino fluorescent species ($C_3$) which has been found to be significantly more fluorescent than the dialkylamino form.

The novel fluorogenic indicator compounds of the present invention have particularly advantageous features. The indicator compounds are essentially nonfluorescent, react quickly with hydrogen peroxide in the presence of a peroxidatively active substance such as peroxidase, are nonreactive with peroxidase alone, and are not interfered with by protein binding. The signal compounds produced upon oxidation are highly fluorescent, have excitation and emission wavelengths above that for background protein fluorescence (e.g., above 390 nm), do not form interfering side products, are stable in the presence of hydrogen peroxide and peroxidatively active substances, and do not exhibit interfering protein binding.

DESCRIPTION OF THE PREFERRED EMBODIMENTS

As used herein, "alkyl" is intended to include aliphatic and cyclic organic residues having a carbon atom at the point of attachment which is bonded to one or more hydrogens or one or more carbons or heterocyclic atoms (e.g., nitrogen, oxygen or sulfur) by single bonds. Accordingly, alkyl groups include the unsubstituted hydrocarbon residues of the formula $-C_mH_{2m+1}$ and substituted and cyclic forms thereof. Such hydrocarbon residues include linear and branched forms and commonly are of the "lower alkyl" aliphatic type wherein m is 6 or less (e.g., methyl, ethyl, n-propyl, iso-propyl, n-butyl, iso-butyl, tert-butyl, n-hexyl, and so forth), but also include higher aliphatic alkyls such as heptyl, octyl, nonyl, and decyl. Alkyl groups also include cycloalkyls such as cyclopentyl, cyclohexyl, cyclooctyl, and so forth. As stated above, alkyl includes substituted residues which are intended to include the hydrocarbon residues bearing one or more, same or different, functional groups or substituents as discussed in detail below which are selected so as not to substantially negate the novel features of the present compounds.

"Aryl", as used herein, is intended to include organic residues derived from an aromatic hydrocarbon or heterocyclic ring or ring system by removal of a hydrogen atom. Accordingly, aryl groups include the unsubstituted hydrocarbon ring residues such as phenyl and naphthyl, and substituted forms thereof. Heterocyclic aryl residues are those comprising one or more heteroatoms (e.g., nitrogen, oxygen, or sulfur) in their ring structure, such as pyridyl, triazoyl, furanyl, imidazolyl, quinolinyl, thiophenyl, thiazolyl, oxazolyl, oxadiazolyl, and pyrimidinyl, and substituted forms thereof. It is understood for the purposes of this invention that aryl residues include those bearing one or more, same or different, functional groups or substituents, as discussed in detail below, which are selected so as not to substantially negate the novel features of the present compounds.

Further, "alkenyl" includes alkyl groups as defined above wherein at least one C—C single bond is replaced with a C—C double bond, and therefore include the unsubstituted lower alkenyls, e.g., vinyl, 1-propenyl, 2-propenyl, and so forth, as well as substituted forms thereof. "Alkoxy" and "aryloxy" intend either linked alkyl and aryl groups, respectively, as defined above (e.g., methoxy, ethoxy, phenoxy). "Carboalkoxy" and "carboaryloxy" intend carboxyl ester linked alkyl and aryl groups, respectively, as defined above (e.g., acetyl, carbethoxy, benzoyloxy). "Carboxamide" intends unsubstituted and mono- or di-N-substituted amido groups.

In the context of the present invention, used herein, an indication that a particular group (e.g., alkyl, aryl, alkenyl, and the like) is substituted is intended to include such groups when mono- or polysubstituted with functional groups which do not substantially negate the novel features of the present compounds. Such functional groups include essentially all chemical groups which can be introduced synthetically and result in stable indicator compounds. Examples of functional groups are hydroxyl, halo (e.g., fluoro, chloro, bromo), amino (including substituted amino such as alkylamino and dialkylamino), cyano, nitro, thiol, carboxyl [including substituted carboxyl such as substituted and unsubstituted esters (carboalkoxy and carboaryloxy) and carboxamides], alkoxy, aryloxy, alkyl, and aryl.

In general, the fluorogenic indicator compounds of the present invention are characterized by having substantially no fluorescent properties or having fluorescent properties, e.g., excitation and/or emission spectra, substantially different from the fluorescent quinoline and coumarin products (B) of the oxidation by hydrogen peroxide. One can screen fluorescent quinolines and coumarins having the general structure of formula (B) for their usefulness in a particular analytical system involving peroxidative oxidation and then modify a selected quinolone or coumarin, or devise a synthetic route, to yield its 3,4-dihydro-derivative (A). There are principally two paths for obtaining a dihydro-compound of the present invention. The first involves direct chemical modification of the fluorophore (B) to reduce the carbon-carbon double bond to a single bond. The second involves a synthesis of the dihydro-compound from nonfluorescent compounds.

The present invention will now be illustrated by particular description of preferred fluorogenic indicators for hydrogen peroxide and their preparation and use. Such indicators have the structure of formula (A) above. Where Y is =O, such compounds are coumarin derivatives, and where Y is =N—$R^8$ are 2-quinolone derivatives.

Particularly preferred indicators are the 7-dialkylamino-2-quinolones of the formula:

(C)

wherein $R^3$ and $R^4$ are alkyl, preferably lower alkyl, and can be prepared by reduction such as with sodium borohydride, of the corresponding known quinolones [German OLS No. 2,363,459]. The ring nitrogen bearing the $R^5$ substituent can be alkylated, if desired, with sodium hydride, followed by an alkyl halide to yield, after reduction, N-substituted dihydroquinolones. Preferably, $R^5$ will be hydrogen or lower alkyl, particularly methyl.

Figure 3:
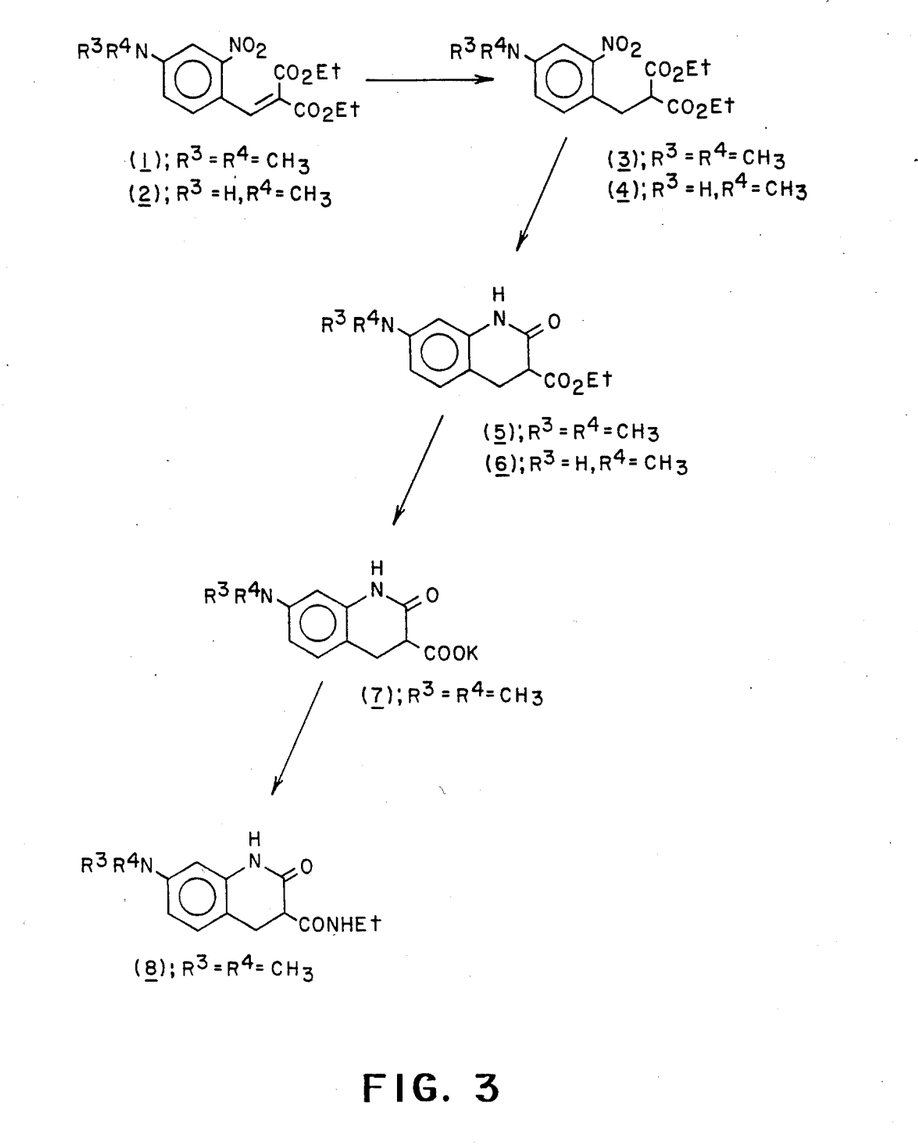
FIGS. 3-6 are flow diagrams of particular synthetic paths for preparing indicator compounds of the present invention.
Figure 4:
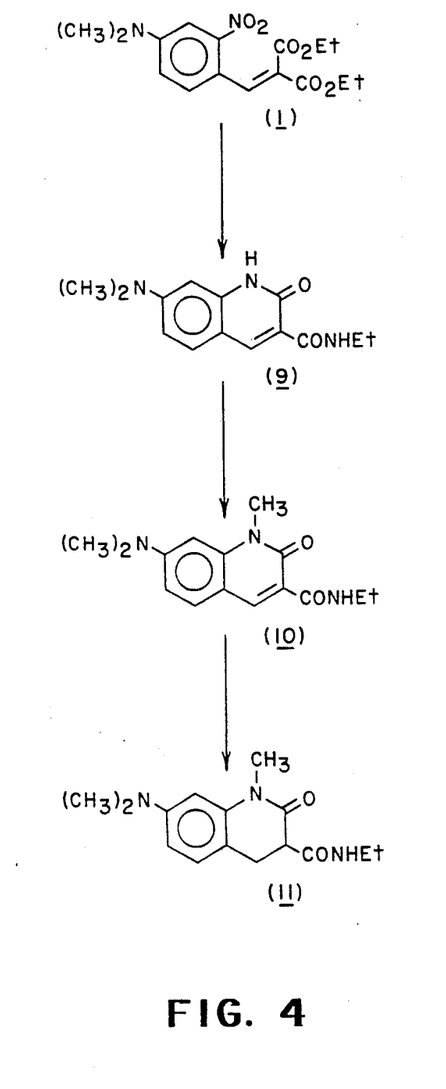

The R¹, substituents can vary widely within the groupings previously described by appropriate selection of the starting quinolone. The dihydroquinolones (C) where R¹ is —COOR⁶, —CONHR⁶, or —CON(R⁶)₂, where R⁶ is hydrogen, alkyl, alkenyl, or aryl, can be prepared from cinnamic diesters of the formula:

(D)

wherein R⁷ is alkyl, alkenyl, or aryl, and preferably is lower alkyl (see FIG. 3). Such cinnamic diesters are prepared by reaction of a 4-disubstituted-amino-2-nitrobenzaldehyde (German Pat. No. 2,363,458) with an appropriate dialkyl-, dialkenyl-, or diaryl malonate. The double bond in the cinnamic diester (D) is reduced, such as with sodium borohydride, then catalytically hydrogenated to reduce the nitro functionality to an aniline intermediate [see compound (5) in FIG. 3] which cyclizes to yield the dihydroquinolone with a —COOR⁷ substituent at the 3-position [the R¹ substituent in formula (C)]. The R¹=COOR⁷ substituent can then be modified by a variety of known methods to provide dihydroquinolones (C) where R¹ is —COOH, —CONHR⁶, or —CON(R⁶)₂. For example, the ester (C), R¹=COOR⁷, can be saponified to yield the carboxylic acid or salt, which can then be condensed with an appropriate amine to yield dihydroquinolones (C) where R¹=CONHR⁶ or CON(R⁶)₂.

Fluorogenic coumarin indicators (A) where Y is oxygen and R² is hydroxyl, i.e., umbelliferone derivatives, can be prepared by reduction of the 3,4-double bond of the appropriate 7-hydroxycoumarin [V. S. Kamat et al, Tett. Lett. 23: 154(1982)] to yield indicator compounds of the formula:

(E)

which upon oxidation by hydrogen peroxide yield the fluorescent coumarins of the formula (F)

by reintroduction of the 3,4-double bond as described previously.

The R¹ substituent can vary widely within the groupings previously described. A wide variety of 3-substituted coumarins [formula (F), R¹=CN, COOC₂H₅, COCH₃, C₆H₅, CONH₂, etc.] are known [W. R. Sherman and E. Robins, Anal. Chem. 40: 803(1968)] or occur naturally in plants ["Heterocyclic Compounds", vol. 2, ed. R. C. Elderfield, John Wiley & Sons (New York 1951) pp. 214-216]. Many such naturally occurring coumarins contain substituents in the benzene ring and others have been made synthetically [J. I. DeGraw et al, J. Med. Chem. 11: 375(1968); J. Banerji et al, J. Chem. Soc. C23: 3992(1971); and M. Bandopadkyay et al, Indian J. Chem. 12: 295(1974)].

Where Y is oxygen and R² is —NR³R⁴, fluorogenic indicators (A) can be prepared by reduction of the appropriate 7-aminocoumarin to yield 7-amino-3,4-dihydrocoumarins of the formula:

(G)

such indicators where R³=R⁴=hydrogen can be obtained by catalytic hydrogenation of the 7-amino or 7-nitrocoumarins. If 7-alkylamino or dialkylamino-3,4-dihydrocoumarins are desired, they can be prepared by N-alkylation of a 7-aminodihydrocoumarin or catalytic hydrogenation of a Schiff base of a 7-aminodihydrocoumarin. Alternatively, the N-alkylaminocoumarin can be prepared using the appropriate 3-alkylaminophenol or 3-dialkylaminophenol as the starting material by the methods described below. The fluorescent species produced upon oxidation by hydrogen peroxide has the formula:

(H)

3-Substituted-7-aminocoumarins can be obtained by Knoevenagel condensation of a 4-amino-2-hydroxy or 2-O-protected benzaldehydes [W. E. Solodar, et al, J. Org. Chem. 23: 103(1958)]; [E. Profft, et al, Arch. Pharm. 300: 1(1967)]; or the Schiff base [A. A. Goldberg, et al, J. Chem. Soc. 2641(1954); H. Ichibagase, J. Pharm. Soc. Jap. 75: 1477(1955); German Pat. No. 1,293,160 (1964) [C. W. Schellhammer, K. W. Mueller, R. Rane)]; with acylacetates or malonic esters. In the O-protected case, deprotection is necessary for cyclization to occur.

Fluorogenic indicators (A) where Y is =NR⁸ and R² is hydroxyl, i.e., 2-quinolone derivatives, can be prepared through the quinolones or cinnamic esters as described above or from the appropriate 7-hydroxy-3,4-dihydro-2-quinolones [N. Shigematsu, Chem. Pharm. Bull. 9: 970(1961)] of the formula:

(J)

Figure 5:
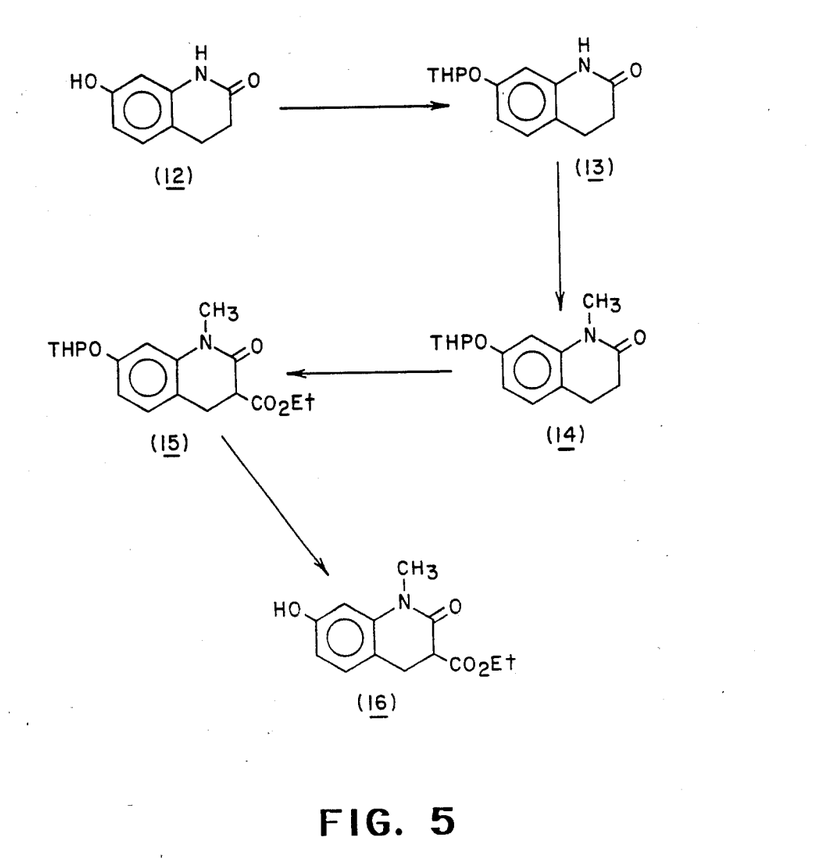

The hydroxyl group is protected in an appropriate manner such as by conversion to its 2-tetrahydropyranyl ether [see compound (13) in FIG. 5]. The protected quinolone can then, if desired, be N-alkylated such as by treatment with an appropriate substituted or unsubstituted alkyl halide and a base such as sodium hydroxide. [N. Shigematsu, supra]. The fluorescent species produced upon oxidation by hydrogen peroxide has the formula:

(K)

(L)

The R[1] substituent can vary widely within the groupings previously described. Reaction of the lactam with a strong base followed by an acylating agent such as diethyl carbonate will introduce a 3-carbethoxy substituent which can be further elaborated to a variety of 3-substituted dihydroquinolones as described previously. Also, the 7-hydroxyl group can be replaced with 7-(lower alkyl) amino substituents, with various derivatives being known [N. Shigematsu, supra; H. Veda and Z. H. Yan, J. Taiwan Pharmaceut. Assoc. 1: 88(1949), Y. Tamura et al, Chem. Ind. (London) 1975, 922; and G. S. Sidhu et al, Annalen 627: 224(1959)].

With reference to formula (A), depicting the general structure of the fluorogenic indicators of the present invention, the R[1] substituent group can vary widely without departing from the inventive features of the present invention. The R[1] substituent generally will be hydrogen, alkyl, normally lower alkyl, alkenyl, normally lower alkenyl, aryl, or an electron withdrawing group. Electron withdrawing groups will be understood to be those groups which increase the acidity of the C-3 protons, with respect to the unsubstituted case, either by an inductive or resonance effect [see J. March, Advanced Organic Chemistry: Reactions, Mechanisms, and Structure, McGraw-Hill (New York) p. 228], and are represented by cyano, carboxyl, carboalkoxy, carboaryloxy, carboxamide, sulfonyl, sulfoxy, sulfonium, phosphonyl, phosphonium, halo, nitro, and aryl. The carboxyl esters are principally alkyl esters such as carbomethoxy, carbethoxy, and so forth, and carboxamide includes substituted amides such as N-alkylcarboxamides and N-aralkylcarboxamides—e.g., N-ethylcarboxamide, N-butylcarboxamide, N-benzylcarboxamide, N-phenethylcarboxamide, and N-2-pyridylmethylcarboxamide. Preferably, R[1] is of the formula —COOR[6], —CONHR[6], or —CON(R[6]) wherein R[6] is hydrogen or substituted or unsubstituted alkyl or aryl. See also the several references cited hereinabove concerning 3-substituted quinolones and coumarins as well as Netherlands Pat. Applns. Nos. 6,603,985 and 6,604,766 and German OLS No. 2,502,588.

It is evident that the 4-, 5-, 6- and 8-positions on the quinolone and coumarin nucleus of the present compounds can bear a variety of substituents without departing from the inventive features of the present indicators. Such substituted forms of the present compounds shall be considered to be equivalents of the present 3,4-dihydro-indicators. One can select essentially any fluorescent quinolone or coumarin, or a quinolone or coumarin providing another useful optical property such as absorbance, and reduce the 3,4-double bond as described herein to yield useful indicator compounds as the formula:

wherein R[1], R[2], and Y are as described above, R[8] and R[9] are essentially any desired substituent groups, and n is an integer from 0 through 3, representing the degree of substitution on the phenyl ring. Commonly, the R[8] substituent would be hydrogen, alkyl, normally unsubstituted lower alkyl or fluorosubstituted lower alkyl (e.g., trifluoromethyl), alkenyl, again normally lower alkenyl, or aryl, all as defined hereinabove. Such desired R[8] substituent can be present in the quinolone or coumarin which is reduced to yield the 3,4-dihyrdo-indicators or can be subsequently introduced or modified by methods available in the literature. 4-Substituted quinolones and coumarins are known [R. M. Forbis et al, JACS 95(15); Canadian Pat. No. 1,088,659; E. R. Bissell et al, J. Org. Chem. 46(12): 2284–7 (1980); and German OLS Nos. 2,502,588 and 2,827,566].

The R[9] substituents can be selected from those known to exist in coumarins and 2-quinolones found in nature or capable of being synthesized to give fluorogenic indicators. The R[9] substituents, if present, (i.e., where n is greater than or equal to 1), occupy the 5-, 6-, and 8-positions on the ring nucleus. When an R[9] substituent is not present at any one or more of such positions, they are occupied by hydrogen. When n=1, the R[9] substituent can be at any of the 4-, 6-, and 8-positions, commonly at the 5- or 6-positions, and preferably at the 6-position. When n=2, the two R[9] substituents can be at the 5- and 6-, the 5- and 8-, or the 6- and 8-positions, and can be the same or different. Such R[9] substituents include halo (fluoro, chloro, bromo), alkyl, normally unsubstituted lower alkyl, alkenyl, again normally unsubstituted lower alkenyl, alkoxy (preferably unsubstituted lower alkoxy such as methoxy and ethoxy), or aryl. In general, the R[9] substituents can include any organic radical or functional group which either enhances or does not significantly negate the fluorescent properties desired in the indicator compound produced and does not interfere with the oxidation process leading to the formation of the fluorescent quinolones and coumarins. Such R[9] substituents can be present in the starting quinolones or coumarins which are reduced to yield the present indicators or can be introduced subsequently (see J. I. DeGraw et al, and M. Bandopadkyay supra). Chemical modification of the aromatic ring can be made by means of Friedel-Crafts reactions [G. A. Olah, Friedel-Crafts and Related Reactions, Interscience Publishers (New York, 1964) vol. 2, part 1]; alkylation of the phenol with an alkyl halide, followed by a Claisen rearrangement [U. Svanholm et al, Chem. Comm. 645(1972)]; or by sulfonation [E. E. Gilbert, Sulfonation and Related Reactions, Interscience Publishers (New York, (1965) pp. 79 and 80].

Figure 6:
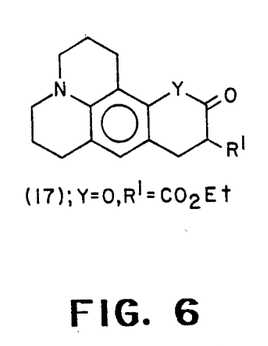

In addition, cycloalkyl, cycloalkenyl, and aryl rings can be annelated to the phenyl ring to yield equivalent substituted indicator compounds, particularly where annelation occurs through the R[2] substituent. For example, where R[2] is nitrogen, one or two R[9] substituents can occupy one or both of the positions adjacent to the R[2] substituent and can be a linear butylene radical forming with $R^2$=nitrogen, one or two tetrahydropyridinyl rings annelated to the phenyl ring (FIG. 6).

A preferred subset of fluorogenic indicators of hydrogen peroxide are those of the formula:

wherein $R^1$ is hydrogen, cyano, or is of the formula —$COOR^6$, —$CONHR^6$, or —$CON(R^6)_2$ where $R^6$ is hydrogen, alkyl, alkenyl, or aryl; $R^2$ is —OH or —$NR^3R^4$ where $R^3$ and $R^4$, which can be the same or different, are hydrogen or lower alkyl; and Y is =O or =N—$R^5$ where $R^5$ is hydrogen or lower alkyl.

The present invention provides particularly advantageous hydrogen peroxide-sensitive indicators for use in analytical systems in the diagnostic field. Numerous diagnostic test systems are known which are based ultimately on the determination of hydrogen peroxide. For example, there are the determinations of various analytes such as glucose, galactose, cholesterol, and uric acid, based on the action of specific oxidase enzymes (e.g., glucose oxidase, galactose oxidase, cholesterol oxidase, uricase). Similarly, there are enzymatic test systems in which the analyte is reacted enzymatically or nonenzymatically to produce a product which in turn is reacted in one or more enzymatic or nonenzymatic steps to yield ultimately hydrogen peroxide.

Furthermore, the present indicators are applicable to specific binding assays such as immunoassays in which a labeling substance is used which is detectable by generation of hydrogen peroxide. Such binding assay systems include those in which the label is an oxidase enzyme or an enzyme which produces a product which is then acted on enzymatically or nonenzymatically to yield hydrogen peroxide. Examples of such systems are the heterogeneous and homogeneous enzymelabeled immunoassays described in the literature such as in U.S. Pat. Nos. 3,654,090 and 3,817,837. Alternatively, the label can be a substrate, an inhibitor, a coenzyme, or a prosthetic group for such an enzyme, as described in U.S. Pat. Nos. 4,279,992; 4,238,565; 4,134,792 and 4,273,866 and in U.K. Pat. Spec. No. 1,552,607.

It is preferred that the test sample or reaction mixture containing hydrogen peroxide to be determined with the present indicator compounds also be contacted with a peroxidatively active substance as is known in the field. Plant peroxidases, such as horseradish peroxidase or potato peroxidase, can be used. Inorganic compounds having peroxidase activity include iodides, such as sodium and ammonium iodides, and molybdates. In addition, urohemin and a number of other porphyrin substances having peroxidative activity can be used.

The present invention will now be illustrated, but is not intended to be limited, by the following examples.

EXAMPLES

Preparation of Fluorogenic Quinolone and Coumarin Indicator Compounds

Italicized numbers in parenthesis refer to the structural formulas in the diagrams in FIGS. 3–6 and are used in the Table at the conclusion of the Examples.

Ethyl-α-carbethoxy-4-dimethylamino-2-nitrocinnamate (1).

A mixture of 8.9 grams (g) [50 millimoles (mmol)] of 4-dimethylamino-2-nitrobenzaldehyde [H. Baumann et al, German Pat. No. 2,363,458], 23.7 g (148 mmol) of diethyl malonate, 3.44 g (40.4 mmol) of piperidine and 2.43 g (40.4 mmol) of acetic acid in 400 milliliters (mL) of toluene was refluxed for 16 hours under argon with a Dean Stark trap attached. The solution was cooled to room temperature and washed with 200 mL of 5% aqueous potassium hydroxide (KOH). The organic phase was separated, dried over sodium sulfate ($Na_2SO_4$), filtered, and the solvent evaporated. The dark red solid residue was dissolved in 40 mL of methylene chloride ($CH_2Cl_2$) and 100 mL of hexane added. After standing for one hour, the solution was filtered to yield 10.4 g of orange crystals. Recrystallization from $CH_2Cl_2$-hexane produced an analytical sample, m.p. 101°–102° C.

Analysis: Calc'd.: $C_{16}H_{20}N_2O_6$: C, 57,14; H, 5.99; N, 8.33. Found: C, 57.65; H, 6.12; N, 8.34.

$^1H$ NMR ($CDCl_3$)δ: 8.08 (s, 1H); 7.3–7.5 (m, 2H); 6.84 (dd, J=3, 8 Hz, 1H); 4,34 (q, J=8, 2H); 4.23 (q, J=8, 2H); 3.10 (s, 6H); 1.27 (q, J=8, 6H).

Ethyl-α-carbethoxy-4-methylamino-2-nitrocinnamate (2).

The cinnamic ester (1) (5.0 g, 14.8 mmol) was dissolved in 100 mL of acetic acid and 7.6 g (17.2 mmol) of lead tetracetate was added. After allowing the mixture to stir for one hour at room temperature, the solvent was removed. Toluene (100 mL) was added and the slurry concentrated, then 100 mL of chloroform ($CHCl_3$) was added, the solid broken up thoroughly, and the solution decanted. Chloroform (100 mL) was added to the solid and the mixture refluxed briefly, filtered, and the filtrate combined with the previous $CHCl_3$ solution. After concentrating the organic solution the residue was chromatographed on 350 g of silica gel eluting with 1:19 (v/v) acetone:$CHCl_3$. Fractions 83–140 (15 mL/fraction) were combined and concentrated to yield the product which was crystallized from $CH_2Cl_2$ (3.45 g, 72%), m.p. 113°–114° C.

Analysis: Calc'd.: $C_{15}H_{18}N_2O_6$: C, 55.90; H, 5.63; N, 8.69. Found: C, 55.57; H, 5.78; N, 8.59.

$^1H$ NMR ($CDCl_3$)δ: 8.00 (s, 1H); 7.33 (d, J=10, 1H); 7.25 (d, J=4, 1H); 6.73 (dd, J=4, 10, 1H); 480 (broad 1, 1H); 4.30 (m, 4H); 2.90 (d, J=5, 3H); 1.30 (q, J=8, 6H).

Ethyl-α-carbethoxy-4-methylamino-2-nitrodihydrocinnamate (4).

Sodium borohydride ($NaBH_4$) (0.2 g, 5.8 mmol) was added to a slurry of the cinnamic ester (2) (3.4 g, 10.5 mmol) in 100 mL of absolute ethanol and the reaction allowed to stir at room temperature for 1.5 hours. Acetic acid (0.5 mL) was added and the mixture concentrated. The residue was dissolved in 250 mL of $CHCl_3$ and was washed with 100 mL of saturated sodium bicarbonate ($NaHCO_3$) solution, and $H_2O$ (100 mL). The organic phase was separated, dried ($Na_2SO_4$) and concentrated to produce 3.1 g of an orange solid. An analytical sample was obtained by crystallization from methanol(MeOH)-water, m.p. 75°–77° C.

Analysis: Calc'd: $C_{15}H_{20}H_2O_6$: C, 55.55; H, 6.21; H, 864. Found: C, 55.34; H, 6.08, H, 8.45.

$H^1NMR$ ($CDCl_3$)δ: 7.2 (m, 2H); 6.70 (dd, J=4,9, 1H); 4.13 (q, J=7, 4H); 3.95–3.20 (m, 3H); 2,86 (d, J=5, 3H); 1.20 (t, J=7, 6H).

7-Dimethylamino-3-carbethoxy-3,4-dihydro-2-quinolone (5).

To a slurry of 5.0 g (14.8 mmol) of the cinnamic ester (1) in 100 mL of absolute ethanol (EtOH) was added 0.34 g (9.2 mmol) of $NaBH_4$. The mixture was allowed to stir for 2.5 hours at room temperature then 1 mL of glacial acetic acid (AcOH) added and the solvent removed under reduced pressure. The residue was dissolved in 250 mL of CHCl$_3$ and washed with 100 mL of saturated NaHCO$_3$ solution. After washing with 100 mL of H$_2$O, the organic phase was dried (Na$_2$SO$_4$), filtered and the solvent evaporated under reduced pressure to yield 4.86 g of the crude dihydrocinnamate (3) as a dark red oil. Dioxane (50 mL) was added and the solution concentrated. The oily residue was dissolved in 50 mL of dioxane and 0.5 g of 10% palladium on charcoal (Pd on C) added. The mixture was shaken under 50 pounds per square inch (psi) of hydrogen gas (H$_2$) at 50° C. for 6.5 hours. After the reaction had cooled to room temperature, the catalyst was removed by filtration through diatomaceous earth (Celite brand, Johns-Manville, Denver, CO) and the solvent concentrated to a volume of 25 mL. Diethyl ether (5 mL) was added and the solution allowed to stand overnight. Filtration produced 2.3 g of the product as a white solid, m.p. 181°–182° C.

Analysis: Calc'd.: C$_{14}$H$_{18}$N$_2$O$_3$: C, 64.10; H, 6.91; N, 10.68. Found: C, 64.45; H, 6,87; N, 11.11.

7-Methylamino-3-carbethoxy-3,4-dihydro-2-quinolone (6).

A mixture of 2.6 g of the diester (4), of 10% Pd on charcoal and 75 mL of dioxane were shaken under 50 psi of hydrogen for 17 hours at 50° C. The catalyst was removed by filtering through Celite and the solvent was removed. The residue was chromatographed on 200 g of silica gel eluting with 3:17 (v/v) acetone: CH$_2$Cl$_2$. Fractions 75-120 (17 mL/fraction) were combined and concentrated to yield 0.5 g of a white powder. Recrystallization from MeOH-H$_2$O produced an analytical sample, m.p. 171°–172° C.

Analysis: Calc'd.: C$_{13}$H$_{16}$N$_2$O$_3$: C, 62,89; H, 6.50; N, 11.28. Found: C, 63,03; H, 6.62; N, 11.54.

$^1$H NMR (D$_6$DMSO)δ: 10.10 (s, 1H); 6,86 (d, J=8, 1H); 6,86 (d, J=8, 1H); 6.10 (m, 2H); 5.57 (broad q, 1H); 4.07 (q, J=7, 2H); 3.49 (t, J=8, 1H); 2.95 (d, J=8, 2H); 2.60 (d, J=5, 3H); 1.15 (t, J=7, 3H).

7-Dimethylamino-3-carboxy-3,4-dihydro-2-quinolone potassium salt (7).

To a slurry of 1.43 g (5.45 mmol) of the ethyl ester (5) in 55 mL of absolute ethanol was added 16 mL (8.3 mmol) of KOH in water. The mixture was allowed to stir for 24 hours at room temperature under argon. The reaction was filtered to yield 1.3 g (84%) of the potassium salt (7) m.p. 193°–195° C.

Analysis: Calc'd.: C$_{12}$H$_{13}$N$_2$O$_3$K.3/4H$_2$O: C, 50.44; H, 5.11; N, 9.80. Found: C, 50.53; H, 5.46; N, 9.82.

7-Dimethylamino-3-(N-ethylcarboxamido)-3,4-dihydro-2-quinolone (8).

A slurry of 1.3 g (4.8 mmol) of the preceeding carboxylate salt (7) in 45 mL of dry dimethyl formamide (DMF) was cooled to 5° C. in an ice bath and 0.72 g (0.68 mL, 5.2 mmol) of isobutyl chloroformate was added dropwise over a three-minute period. The reaction was allowed to warm to room temperature and stir for 15 minutes. Then, 6 mL of ethylamine, which had been distilled previously and stored over sodium hydroxide (NaOH), in 15 mL of DMF was added rapidly. After stirring for two hours the solution was concentrated and the residue chromatographed on 150 g of silica gel, eluting with 1:19 (v/v) CH$_3$OH:CH$_2$Cl$_2$. Fractions 45-75 (12 mL/fraction) contained the amide (8) which crystallized from diethyl ether-hexane, to yield 0.2 g of a white solid, m.p. 216°–218° C.

Analysis: Calc'd.: C$_{14}$H$_{19}$O$_2$N$_3$: C, 64.35; H, 7.33; N, 16.08. Found: C, 64.97; H, 7.78; N, 16.24.

$^1$H NMR δ: 8.10 (broad s, 1H); 7.60 (broad, 1H); 7.05 (d, J=9, 1H); 7.05 (d, J=9, 1H); 6.33 (dd, J=4, 9, 1H); 6.07 (d, J=4, 1H); 3.60-3.20 (m, 5H); 2.90 (s, 6H); 1.13 (t, J=7, 3H).

7-Dimethylamino-3-(N-ethylcarboxamido)-2-quinolone (9).

A mixture of 1.0 g (3.0 mmol) of the cinnamic ester (1), 40 mL of absolute EtOH, 1 mL of H$_2$O, 0.4 mL of concentrated hydrochloric acid (HCl), and 1.5 g (26.9 mg-atom) of iron filings was refluxed with vigorous stirring, under argon, for 2.5 hours. An additional 1.7 g (30.4 mg-atom) was added and the heating continued for three hours. The mixture was filtered while hot and the filtrate evaporated. The residue was dissolved in 50 mL of 2.55M methanolic HCl and allowed to stand for 20 minutes at room temperature, then solvent was evaporated and the residue partitioned between 150 mL of CHCl$_3$ and 50 mL of saturated NaHCO$_3$ solution. The organic phase was separated and the aqueous phase washed with 75 mL of CHCl$_3$. The organic phases were combined, dried (Na$_2$SO$_4$), filtered and concentrated to yield 0.49 g of a dark brown solid. The aqueous phase was extracted with 120 mL of isobutanol, which when dried (Na$_2$SO$_4$), filtered, and evaporated produced an additional 0.08 g. The two residues were combined and slurried in 30 mL of MeOH and 10 mL of 70% ethylamine (EtNH$_2$)-30% H$_2$O were added. The mixture was stirred for three days at room temperature, then was placed in a stainless steel bomb and heated at 100° C. for six hours. After evaporation of the solvent, the residue was chromatographed on 75 g of silica gel, eluting with 19:1 (v/v) CH$_2$Cl$_2$:MeOH. Fractions 25-34 (7 mL/fraction) were combined and concentrated to a volume of 7 mL. Filtration yielded 0.19 g of yellow needles, m.p. 299°–300° C.

Analysis: Calc'd.: C$_{14}$H$_{17}$N$_3$O$_2$: C, 74.85; H, 6.61; N, 16.20. Found: C, 74,84; H, 6.74; N, 16.19.

$^1$H NMR (CDCl$_3$)δ: 7.53 (d, J=9, 1H); 6.60 (dd, J=4, 9, 1H); 6.40 (broad m, 1H), 3.53 (m, 2H); 3.10 (s, 6H); 1.25 (t, J=7, 3H).

7-Dimethylamino-3-(N-ethylcarboxamido)-1-methyl-2-quinolone (10).

A 50% oil dispersion of sodium hydride (10 mg, 0.2 mmol) was washed twice with hexane and 1 mL of dioxane added. To the slurry was added 50 mg (0.2 mmol) of the quinolone (9) in 2 mL of a 1:1 mixture of dioxane/DMF. The mixture was allowed to stir for 30 minutes at room temperature, then 0.56 g (4 mmol) of iodomethane was added rapidly. After allowing the solution to stir for 30 minutes, the solvent was evaporated and the residue dissolved in 50 mL of CHCl$_3$. The solution was washed with 30 mL of H$_2$O and the organic layer was dried (Na$_2$SO$_4$), filtered, and evaporated. Precipitation of the product occurred when the residue was dissolved in 5 mL of CHCl$_3$ and triturated with 20 mL of diethyl ether. Filtration yielded 32 mg of a yellow solid, m.p. 248°–250° C. Recrystallization from ethanol provided yellow needles, m.p. 252°–253° C.

Analysis: Calc'd.: C$_{15}$H$_{21}$N$_3$O$_2$: C, 75.09; H, 7.00; N, 15.37. Found: C, 75.08; H, 6.93; N, 15,31.

$^1$H NMR (CDCl$_3$)δ: 8.40 (s, 1H); 7.58 (d, J=9, 1H); 6.68 (dd, J=4, 9, 1H); 6.23 (s, 3H); 3,2-3.7 (m, 2H); 3.13 (s, 6H); 1.26 (t, J=8, 3H).

7-Dimethylamino-3-(N-ethylcarboxamido)-3,4-dihydro-1-methyl-2-quinolone (11).

A mixture of 0.3 g (1.15 mmol) of the preceeding 2-quinolone (10) and 0.1 g (2.6 mmol) of NaBH$_4$ in 25 mL of absolute EtOH was allowed to stir for 24 hours. An additional 0.1 g of NaBH$_4$ was added and the reaction allowed to stir overnight at room temperature. Again, 0.1 g of NaBH$_4$ was added and the reaction heated at 70° C. for 24 hours, then 0.3 g of NaBH$_4$ was added and the heating continued for 24 hours. The solvent was evaporated and the residue chromatographed on 100 g of silica gel, eluting with 2.5% (v/v) MeOH:CH$_2$Cl$_2$. Fractions 55–85 (12 mL/fraction) were combined and concentrated to yield 0.14 g of the dihydroquinolone as a pale yellow solid, m.p. 105°–107° C.

Analysis: $^1$H NMR (CDCl$_3$)δ: 7.10 (d, J=8, 1H); 6.33 (s, 1H); 3.40 (s, 3H); 3.24 (m, 5H); 2.97 (s, 6H); 1.18 (t, J=8, 3H).

7-Hydroxy-3-carbethoxy-3,4-dihydro-1-methyl-2-quinolone (16).

To a slurry of 1 g of 7-hydroxy-3,4-dihydro-2-quinolone (12) [N. Shigematsu, Chem. Pharm. Bull. 9: 970 (1961)] in 8 mL of dry dioxane was added 8 mL of dihydropyran and 5 mg of p-toluene sulfonic acid. The reaction was stirred under an inert atmosphere for 90 minutes, then diluted with 150 mL of H$_2$O. It was extracted with three 50 mL portions of ether, and the combined extracts dried over anhydrous potassium carbonate (K$_2$CO$_3$). Filtration and evaporation gave 2 g of an oil which crystallized when triturated with hexane. When dry it amounted to 1.18 g (78%) of white crystals of the 2-tetrahydropyranyl ether (13), m.p. 129°–131° C.

A slurry of 2.47 g (10 mMol) of (13) and 228 mg of benzyltriethylammonium chloride in a mixture of 50 mL of toluene and 4 mL of a solution of 1 g of NaOH in 1 mL of H$_2$O was stirred under an inert atmosphere at room temperature. Methyl iodide (1.26 mL mmol) was added and the reaction stirred rapidly for 20 hours at 47° C. (oil bath). It was then diluted with 250 mL portions of CHCl$_3$. The CHCl$_3$ extracts were combined with the toluene phase, dried and evaporated. The oil residue was crystallized from hexane to give 2.56 g (93%) of (14) as a white solid m.p. 53°–55° C.

A solution of 0.315 mL of freshly distilled isopropylcyclohexylamine in 2 mL of dry tetrahydrofuran (THF) was placed in a 25 mL flask. A second solution was prepared by dissolving 0.315 mL of the same amine in 1.5 mL of THF in a 5 mL flask. Both solutions were cooled to −78° C. while stirring under an inert atmosphere and treated with 1.2 mL of a 1.6 mL of a 1.6M hexane solution of n-butyllithium, dropwise from a syringe over 1.5 minutes in order to form lithium isopropylcyclohexylamide. To the first solution was added, dropwise over six minutes, 500 mg of (14) in 1 mL of THF. The reaction was stirred at −78+ C. for five minutes, then a solution of 0.12 mL of diethyl carbonate in 0.5 mL of THF was added, dropwise over ten minutes via syringe. After three additional minutes, the second solution of lithium isopropylcyclohexylamide was added followed by an additional 0.12 mL of diethyl carbonate. After 20 minutes at −78° C., the reaction was allowed to warm to room temperature and stir for ten minutes following which it was neutralized with 0.2 mL of acetic acid in 2 mL of H$_2$O. The reaction was partitioned between 100 mL of H$_2$O and 35 mL of ether. The ether phase was separated, dried, filtered, evaporated, and the residue dried under high vacuum to give a yellow oil. It was chromatographed on 60 g of silica gel eluting with 29:1 [v/v] CH$_2$Cl$_2$:EtOH. Nine mL fractions were collected. Fractions 29–51 were combined and evaporated to give 548 mg (86% yield) of the ester (15) as a clear pale-yellow oil.

A solution of the tetrahydropyranyl ether (15) in 3:1 (v/v) AcOH:H$_2$O was allowed to stir at room temperature for 17 hours. The mixture was concentrated and 10 mL of toluene added and then evaporated to yield a white solid, m.p. 121°–123° C.

Analysis: Calc'd.: C$_{13}$H$_{15}$NO$_3$: C, 62.64; H, 6.07; N, 5.62. Found: C, 62.98; H, 6.25, N, 5.27.

$^1$H NMR (CDCl$_3$)δ: 7.45 (broad, 1H); 7.05 (d, J=8, 1H); 6.67 (s, 1H); 6.57 (dd, J=2, 8, 1H); 4,20 (t, J=7, 2H); 3,40 (s, 3H); 3.8–3.0 (m, 3H); 1.20 (q, J=7, 3H).

[2,3,6,7,9,10]-Hexahydro-10-carbethoxy-11-oxo-1H,5H,11H-[1]benzopyran[6,7,8-ij]quinolizine (17).

A mixture of coumarin 314 (Eastman Organic Chemicals, 0.1 g), 0.05 g of 10% Pd/C and 25 mL of acetic acid was placed under 50 psi of hydrogen at 50° C. and shaken for 24 hours. The catalyst was removed by filtering through Celite and the solution concentrated. The brown residue was chromatographed on 40 g of silica gel, eluting with 1019 (v/v) acetone:methylene chloride. Fractions 3–17 (15 mL/fraction) were combined and concentrated under vacuum. The product crystalized from methylene chloride-hexane to yield 0.03 g of white needles, m.p. 141°–143° C.

Analysis: Calc'd: C$_{18}$H$_{21}$O$_4$N: C, 68.61; H, 6.71; N, 4.44. Found: C, 68.25; H, 6.96; N, 4.49.

Compounds of the general formula shown in FIG. 6 can be prepared for R$^1$=hydrogen, cyano, or —COOR$^6$, —CONHR$^6$, —CON(R$^6$)$_2$ where R$^6$ is hydrogen, alkyl, alkenyl, or aryl and Y=O or N—R$^5$ where R$^5$ is hydrogen or lower alkyl by selecting the appropriate starting coumarin or 2-quinolone.

7-Dimethylamino-3,4-dihydro-2-quinolone.

To a solution of 1.0 g (5.7 mmol) of 7-dimethylamino-2-quinolone [A. Rice, Ann. Chim. 48: 958–996(1958)] in 40 mL of MeOH was added 1.3 g (5.7 mmol) of magnesium. The reaction was warmed gently on a steam bath, and then was allowed to stir for two hours at room temperature. Acetic acid (8 mL) was then added and the solution filtered. The filtrate was concentrated and the residue chromatographed on 200 g of silica gel, eluting with 97.5:2.5 (v/v) CH$_2$Cl$_2$:MeOH. Fractions 50–60 (12 mL/fraction) were combined and concentrated to yield 0.4 g of the dihydroquinolone as a white solid, m.p. 154°–156° C.

Analysis: $^1$H NMR (CDCl$_3$)δ: 7.00 (d, J=8, 1H); 6.40 (dd, J=2.8, 1H); 6.13 (d, J=2, 1H); 2.93 (s, 6H); 2.73 (m, 4H).

Detection of Hydrogen Peroxide

A 1.0 μM, pH 7.0 or 7.5, sodium phosphate buffer solution of the dihydroquinolones and dihydrocoumarins listed in the Table below were prepared by successive dilutions with the buffer of an ethanol or DMF-ethanol solution of the appropriate compound. The solution was warmed in a 37° C. bath, then a 40 microliter (μL) of 1 mg/mL horseradish peroxidase enzyme was added in one portion. The contents of the cuvette were mixed and the fluorescence was monitored for at least 50 seconds (the quartz cell and its contents were held at a constant 37° C.). A quantity of hydrogen peroxide diluted in cold water and stored at 0° for less than eight hours was then added in an amount suitable for the desired ratio of dihydroquinolone to peroxide. The fluorescence was then monitored over a 600 second time span. Fluorescent values for compounds (5), (6), (7), (11), (16), and (17) were reported in units of concentration (nM) of the flourescent standard 7-hydroxy-3-(N-ethylcarboxamido) coumarin (U.S. Pat. No. 4,273,715) which would be required to achieve the same fluorescence light output as the subject of study. Compound (8) is reported in photons/second. All slit widths were set at 2 nm (nanometers).

Fluorescence was measured in quartz cuvettes on an SLM 8000 spectrofluorometer (SLM Instruments, Inc. Urbana, Ill.). A Hewlett-Packard 8915A computer was used to process spectra.

The results are given in Table 1 and demonstrate that compounds of the present invention provide useful fluorescent responses to the presence of hydrogen peroxide.

Obviously, many other variations and modifications of the invention as set forth above may be made without departing from the spirit and scope hereof.

wherein $R^1$ is hydrogen, cyano, or —$COOR^6$, —$CONHR^6$ or —$CON(R^6)_2$ wherein $R^6$ is hydrogen, alkyl, alkenyl, or aryl; $R^3$ and $R^4$, which can be the same or different, are lower alkyl; and $R^5$ is hydrogen or lower alkyl.

8. The method of claim 7 wherein $R^3$ and $R^4$ are both methyl.

9. The method of claim 8 wherein $R^1$ is 13 $COOR^6$, —$CONHR^6$ or —$CON(R^6)_2$.

10. The method of claim 9 wherein $R^5$ is hydrogen or

TABLE 1

| | | | Relative Fluorescence of Indicator Compounds (nM) | | | | | |
|---|---|---|---|---|---|---|---|---|
| | Excitation | Emission | Fluorescence Units | | | | | |
| Compound | Wavelength (nm) | Wavelength (nm) | 0 secs | 25 secs | 50 secs | 100 secs | 200 secs | 600 secs |
| (5) | 400 | 450 | 1.4 | 81.5 | — | 101.5 | 101.5 | 101.25 |
| (6) | 400 | 450 | <0.12 | 4.0 | 8.75 | 11.0 | 11.25 | 10.8 |
| (7) | 366 | 435 | 1.4 | 12.3 | — | 22.2 | 24.3 | 24.6 |
| (8) | 400 | 450 | <428 | 20,142 | 27,000 | 29,000 | 30,000 | 30,000* |
| (11) | 400 | 450 | 4.3 | 8.9 | — | 101.5 | 133.5 | 142.5 |
| (16) | 400 | 450 | 1.3 | 4.3 | — | 5.7 | 6.3 | 6.3 |
| (17) | 402 | 472 | 0.6 | 8.8 | — | 13.0 | 25.9 | 42.5 |

*photons/second

What is claimed is:

1. A method for determining hydrogen peroxide comprising the steps of (a) contacting a test sample in the presence of a peroxidatively active substance with a compound of the formula:

wherein $R^1$ is hydrogen, alkyl, alkenyl, aryl, or an electron withdrawing group; $R^2$ is hydroxyl or —$NR^3R^4$ where $R^3$ and $R^4$, which can be the same or different, are hydrogen, alkyl, alkenyl, or aryl; and Y is =O or =N—$R^5$ where $R^5$ is hydrogen or lower alkyl; and (b) measuring the fluorescence of a product resulting from oxidation of said compound by hydrogen peroxide.

2. The method of claim 1 wherein the peroxidatively active substance is peroxidase.

3. The method of claim 1 wherein $R^2$ is —$NR^3R^4$ and $R^3$ and $R^4$ are both lower alkyl.

4. The method of claim 3 wherein $R^2$ is —$NR^3R^4$ and $R^3$ and $R^4$ are both methyl.

5. The method of claim 3 wherein Y is =N—$R^5$.

6. The method of claim 1 wherein $R^1$ is hydrogen, alkyl, alkenyl, aryl, cyano, carboxyl, carboalkoxy, carboaryloxy, carboxamide, sulfonyl, sulfoxy, sulfonium, phosphonyl, phosphonium, halo, or nitro.

7. The method of claim 1 wherein the compound is of the formula:

methyl.

11. A test composition for determining hydrogen peroxide in a test sample comprising (a) a compound of the formula:

wherein $R^1$ is hydrogen, alkyl, alkenyl, aryl, or an electron withdrawing group; $R^2$ is hydroxyl or —$NR^3R^4$ where $R^3$ and $R^4$, which can be the same or different, are hydrogen, alkyl, alkenyl, or aryl; and Y is =O or =N—$R^5$ where $R^5$ is hydrogen or lower alkyl; and (b) a peroxidatively active substance.

12. The test composition of claim 11 wherein the peroxidatively active substance is peroxidase.

13. The test composition of claim 11 wherein $R^2$ is —$NR^3 R^4$ and $R^3$ and $R^4$ are both lower alkyl.

14. The test composition of claim 13 wherein $R^3$ and $R^4$ are both methyl.

15. The test composition of claim 13 wherein Y is =N—$R^5$.

16. The test composition of claim 11 wherein $R^1$ is hydrogen, alkyl, alkenyl, aryl, cyano, carboxyl, carboalkoxy, carboaryloxy, carboxamide, sulfonyl, sulfoxy, sulfonium, phosphonyl, phosphonium, halo, or nitro.

17. The test composition of claim 11 wherein the compound is of the formula:

wherein $R^1$ is hydrogen, cyano, or —$COOR^6$, —$CONHR^6$ or —$CON(R^6)_2$ where $R^6$ is hydrogen, alkyl, alkenyl, or aryl; $R^3$ and $R^4$, which can be the same or different, are lower alkyl; and $R^5$ is hydrogen or lower alkyl.

18. The test composition of claim 17 wherein $R^3$ and $R^4$ are both methyl.

19. The test composition of claim 18 wherein $R^1$ is —$COOR^6$, —$CONHR^6$ or —$CON(R^6)_2$.

20. The test composition of claim 19 wherein $R^5$ is hydrogen or methyl.

* * * * *

UNITED STATES PATENT AND TRADEMARK OFFICE
CERTIFICATE OF CORRECTION

PATENT NO. : 4,794,079
DATED : December 27, 1988
INVENTOR(S) : Robert T. Buckler et al.

It is certified that error appears in the above-identified patent and that said Letters Patent is hereby corrected as shown below:

In col. 4, line 2, read -- ether -- for "either".

In col. 10, line 43, read -- broad q -- for "broad 1".

Signed and Sealed this

Third Day of October, 1989

*Attest:*

DONALD J. QUIGG

*Attesting Officer*  *Commissioner of Patents and Trademarks*